US012631474B2

(12) United States Patent
Ruohio

(10) Patent No.: US 12,631,474 B2
(45) Date of Patent: May 19, 2026

(54) MITIGATING SYSTEMATIC ERROR IN GYROCOMPASSING

(71) Applicant: Murata Manufacturing Co., Ltd., Nagaokakyo (JP)

(72) Inventor: Jaakko Ruohio, Helsinki (FI)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 295 days.

(21) Appl. No.: 18/484,878

(22) Filed: Oct. 11, 2023

(65) Prior Publication Data

US 2024/0133713 A1 Apr. 25, 2024

(30) Foreign Application Priority Data

Oct. 14, 2022 (EP) ..................................... 22201581

(51) Int. Cl.

| | |
|---|---|
| *G01C 19/38* | (2006.01) |
| *G01C 19/58* | (2006.01) |
| *G01C 25/00* | (2006.01) |
| *G01N 33/49* | (2006.01) |

(52) U.S. Cl.
CPC ............. *G01C 25/00* (2013.01); *G01C 19/58* (2013.01); *G01N 33/491* (2013.01)

(58) Field of Classification Search
CPC ........ G01C 25/00; G01C 19/58; G01C 17/38; G01C 19/38; G01N 33/491
USPC ........ 73/1.37, 1.75, 1.77, 503.3; 702/85, 87, 702/89, 93; 701/530
See application file for complete search history.

(56) References Cited

U.S. PATENT DOCUMENTS

| | | |
|---|---|---|
| 2021/0348502 A1 | 11/2021 | Xue et al. |
| 2023/0204358 A1* | 6/2023 | Aaltonen ............... G01C 19/38 |
| | | 33/318 |

FOREIGN PATENT DOCUMENTS

WO WO-2022090955 * 5/2011

OTHER PUBLICATIONS

Wu, Zheming et al.; "Attitude and gyro bias estimation by the rotation of an inertial measurement unit"; Measurement Science and Technology, vol. 26, 2015, 9 pages.
Wahlstroem, Johan et al.; "Fifteen Years of Progress at Zero Velocity: A Review"; arXiv:2008.09208v1, retrieved from https://arxiv.org, Aug. 20, 2020, 13 pages.

* cited by examiner

*Primary Examiner* — Robert R Raevis
(74) *Attorney, Agent, or Firm* — ArentFox Schiff LLP

(57) ABSTRACT

A MEMS gyrocompass and method are provided to mitigate systematic error in determination of a north angle. The MEMS gyrocompass includes one or more MEMS gyroscopes having a sense axis within a reference plane. Samples from an output of the MEMS gyroscope are obtained in at least two angles of rotation about an axis perpendicular to the reference plane. First fit coefficients are determined by fitting samples with first fitting functions determined as function of time. Second fit coefficients are determined by fitting components of earth rotation rate projected on the reference plane based on samples obtained by all the MEMS gyroscopes, which fitting is performed with a second fitting function determined as a function of rotation angle of the MEMS gyroscope with respect to a reference angle. The north angle is determined as an angle between the reference angle and true north based on the second fit coefficients.

20 Claims, 13 Drawing Sheets

MITIGATING SYSTEMATIC ERROR IN GYROCOMPASSING

CROSS REFERENCE TO RELATED APPLICATIONS

This application claims priority from European patent application 22201581.0, filed on Oct. 14, 2022, the entire contents of which are hereby incorporated by reference.

TECHNICAL FIELD

The present invention relates to a method, a system and a computer program product related to gyrocompassing. More particularly, the invention relates to a method of mitigating systematic error in north angle determined by a gyrocompass.

BACKGROUND

Measuring horizontal rotation rate of the Earth reveals the direction to the geographic (true) north. This is called gyrocompassing, or north finding. A determined direction to the geographic north is often referred to as the north angle, describing offset angle between a reference direction and the true north. At the equator, the horizontal rotation rate of the Earth is approximately 360°/day=15°/h=4.178 mdeg/s (milli-degrees per second), whereas it vanishes at the poles as the cosine of the latitude (cos θ). Magnetic compasses point to the magnetic north determined by the Earth's magnetic field, which differs from the geographic north. Also, magnetic compasses suffer from magnetic disturbances caused for example by presence of magnetic material, magnetic fields caused by electric current and/or by changes in the Earth's magnetic field.

Gyrocompassing poses significant requirements on gyroscope performance.

Allan deviation is used to study the output stability of instruments in the time domain, revealing properties of different noise contributions. For example, Allan deviation is used as indicating output stability of devices such as frequency of an oscillator, output bias of an accelerometer, and output bias of and also more generally the output stability of a gyroscope.

The Allan deviation of a time domain signal consists of computing its Allan deviation as a function of different averaging times r and then analyzing the characteristic regions and log-log scale slopes of the Allan deviation curves to identify the different noise modes.

FIG. 1 shows an exemplary Allan deviation (ADEV) plot of an output of a gyroscope in which output angular rate is dominated by phenomena known as angular random walk (ARW), bias instability (B) and rate random walk (RRW). The term angular random walk refers to effect of white noise component perturbing output of the gyroscope. Allan deviation (ADEV) due to rate random walk (RRW) is largest during warm-up period of the gyroscope and reduces over time. Smallest achievable values of the Allan deviation are typically limited by bias instability (B), which is not dependent on time. Bias instability (B) can be characterized as 1/f noise, also referred to as pink noise, in other words low frequency noise for which the noise power is inversely proportional to the frequency, and in practice present in most physical devices and systems. When the exemplary gyroscope is used over extensive periods, the Allan deviation (ADEV) is dominated by rate random walk (RRW) caused bias fluctuations caused in the long term, primarily due to temperature effects.

FIG. 2 shows another exemplary Allan deviation plot of a gyroscope output in which error in the output is dominated by angular random walk (ARW) and rate drift (RR). Rate drift (RR) is primarily caused by bias instability, but unlike bias instability (B), rate drift is dependent on time and can dominate at large integration time periods: the longer the integration period, the stronger the error caused by the rate drift (RR).

In the example of the FIG. 2, the rate drift (RR) starts to dominate the output already at relatively short integration times. Sources of rate drift (RR) are many, for example changes in quadrature error, sense resonator phase changes, frequency shifts, insulator charging, changes in metal electrode work function, mechanical stress, electrostatic softening changes, temperature changes, temperature gradients, and so on.

Total rate drift generated systematic error of north angle of a gyrocompass can be heuristically expressed as:

$$\alpha |\Sigma_j RR_j e^{i\varphi_j}| \tag{1}$$

Where $\varphi_j$ is gyroscope j sense axis angle with respect to a reference axis and $RR_j$ is the rate drift of the gyroscope j.

FIGS. 3 to 4 illustrate angle error of one gyroscope as a function of north angle. In the FIG. 3, the sense axis angle $\varphi_1=0°$, and linear rate drift is 0.1 mdps/s, which corresponds to case #12 in the table 1 for a single gyroscope. In this graph north angle reflects offset of the sense axis from the true north, which changes over time as the gyroscope is rotated by the turn table. North angle error is zero at rotation angles 135° and 315°, while worst-case error is 1.22° at angles 46.2° and 223.8°.

FIG. 4 illustrates north angle error of another gyroscope with a sense axis angle $\varphi_2=90°$, and linear rate drift is the same 0.1 mdps/s. North angle error is zero at angles 45° and 225°, while worst-case error is 1.22° at angles 136.2° and 313.8°.

FIG. 5 illustrates north angle error received from two gyroscopes with sense axis angles ($\varphi_1=0°$ and $\varphi_2=90°$, both having linear rate drift at 0.1 mdps/s. North angle error is zero at angles 0° and 180°. Worst-case error 1.72° occurs at angles 91.7° and 268.3°.

Rate drift (RR) tends to vary between gyroscopes, even if gyroscopes were essentially similar. In a gyrocompassing apparatus that uses a plurality of similar gyroscopes for determining direction of true north, rate drift (RR) causes a systematic error in the north reading unless effects of rate drift (RR) can be mitigated.

Effects of angular random walk (ARW) can be mitigated by increasing integration time, which effectively reduces effects of white noise in the output. However, very long integration times not only increases risk of rate drift (RR) but also causes delay in receiving the wanted indication of true north direction. As explained above, rate drift (RR) puts an upper limit for applicable integration times. As seen in the FIGS. 1 and 2, the exemplary system would require an integration time of about 100 seconds or more to obtain the best results, which is not an acceptable delay in time-sensitive applications.

The table 1 below illustrates systematic error caused by rate drift in a gyrocompass with different numbers of gyroscopes. In a computer simulation, a simulated board with gyroscopes was rotated with a turn table by 1 full rotation (360 degrees) in 10 seconds. Sampling frequency used was 10 Hz and duty cycle was 40%, in other words 40% of total time was used for sampling. No rate drift fitting function was applied. It should be noted that systematic error does not depend on total measurement time or sampling frequency, but systematic error depends on duty cycle.

TABLE 1

| # | Number of gyroscopes | Linear rate drift (mdps/s) | Max systematic north angle error (deg) |
|---|---|---|---|
| 1 | 1 | 0 | 0 |
| 2 | | +0.1 | 4.87 |
| 3 | | +0.2 | 9.77 |
| 4 | 2 (0, 90) | 0, 0 | 0 |
| 5 | | +0.1, 0 | 2.43 |
| 6 | | +0.1, +0.1 | 3.44 |
| 7 | 2 (0, 180) | 0, 0 | 0 |
| 8 | | +0.1, 0 | 2.43 |
| 9 | | +0.1, +0.1 | 0 |
| 10 | | +0.1, −0.1 | 4.87 |
| 11 | 4 (0, 180, 90, | 0, 0, 0, 0 | 0 |
| 12 | 270) | +0.1, 0, 0, 0 | 1.22 |
| 13 | | +0.1, +0.1, 0, 0 | 0 |
| 14 | | 0, 0, +0.1, +0.1 | 0 |
| 15 | | +0.1, −0.1, +0.1, −0.1 | 3.44 |

It is noted that table 1 illustrates the results of computer simulations performed with the invented fitting method using a testbed with one to four gyroscopes For testing purposes, set values of linear rate drift was caused for the gyroscopes in computer simulation as defined in the table 1. With a single gyroscope, cases #1 to #3 in the table 1, systematic error in north angle increases with increasing rate drift.

A two-gyroscope system was tested with two different setups, first with a 90-degree angle between sense axes of the two gyroscopes (cases #4 to #6) and then with a 180-degree angle between sense axes of the two gyroscopes (cases #7 to #10). Cases #5 and #6 show that in presence of rate drift, the 90-degree angle setup is not able to remove the systematic error, even if results are improved in comparison to the single gyroscope case. With two gyroscopes having 180-degree angle between sense axes thereof, rate drift can be fully compensated without fitting if rate drift of both gyroscopes is mutually similar and in the same direction, as shown in cases #13 and #14, but if rate drifts of opposite-facing gyroscopes are mutually different as in cases #12 and #15, systematic error remains. However, in this setup, systematic error is half in magnitude in comparison to the single-gyroscope case. Having two gyroscopes with 180 degrees between sense axis thereof creates a setup that has a considerable degree of similarity to a maytagging operation in which a single gyroscope is flipped 180 degrees for removing offset. However, because there are two different gyroscopes, these may have mutually different performance characteristics, including mutually different rate drifts, in which case significant systematic error will remain in the output.

With four gyroscopes installed in relative sense axis angles $\varphi_i = \{0°, 180°, 90°, 270°\}$, cases #11 to #15 in the Table 1, systematic error caused by rate drift can be cancelled whenever a pair of gyroscopes having sense axis in mutually opposite directions (180° offset) have mutually similar rate drift. However, in any other case some systematic error remains in the north angle in presence of rate drift.

SUMMARY OF THE INVENTION

In view of the foregoing, it is an object of the present invention to provide a method and apparatus to mitigate systematic error caused by mutually different offset drifts of gyroscopes in a MEMS gyrocompass.

According to an exemplary aspect, a method is provided for mitigating systematic error in north angle determined by a MEMS gyrocompass comprising at least one MEMS gyroscope having a sense axis within a reference plane is provided. The method includes obtaining samples from the output of the at least one MEMS gyroscope in at least two different angles of rotation about an axis perpendicular to the reference plane, determining one or more first fit coefficients by fitting samples obtained from each individual MEMS gyroscope with first fitting functions determined as function of time, determining second fit coefficients by fitting components of earth rotation rate projected on the reference plane based on samples obtained from all of the at least one MEMS gyroscope with a second fitting function determined as function of rotation angle of the at least one MEMS gyroscope with respect to a reference angle, and determining the north angle as an angle between the reference angle and true north based on the second fit coefficients.

According to another exemplary aspect, the first fitting function is a rate drift fitting function, which is one of a first order function, a second order function, an exponential function and a sum of exponential functions.

According to another exemplary aspect, the first fit coefficients are determined individually to each MEMS gyroscope.

According to another exemplary aspect, the second fit coefficients are a cosine coefficient (c) and a sine coefficient (s), and wherein the north angle is calculated by arctan(s/c).

According to another exemplary aspect, the number of MEMS gyroscopes is at least two, and MEMS gyroscopes are arranged such that vector sum of sense axes of the MEMS gyroscopes is zero.

According to another exemplary aspect, the determination of the first fit coefficients and the second fit coefficients are performed simultaneously.

According to yet another exemplary aspect, a MEMS gyrocompass is provided that is configured to mitigate systematic error in determination of a north angle is provided. The MEMS gyrocompass comprises at least one MEMS gyroscope having a sense axis within a reference plane. The MEMS gyrocompass can include a processing device and execute instructions on memory that configure the MEMS gyrocompass to obtain samples from an output of the at least one MEMS gyroscope in at least two angles of rotation about an axis perpendicular to the reference plane, to determine one or more first fit coefficients by fitting samples obtained from each individual MEMS gyroscope with first fitting functions determined as function of time, to determine second fit coefficients by fitting components of earth rotation rate projected on the reference plane based on samples obtained by all of the at least one MEMS gyroscope, wherein said fitting is performed with a second fitting function determined as a function of rotation angle of the at least one MEMS gyroscope with respect to a reference angle, and to determine the north angle as an angle between the reference angle and true north based on the second fit coefficients.

According to another exemplary aspect, the first fitting function is a rate drift fitting function, which is one of a first order function, a second order function, an exponential function and a sum of exponential functions.

According to another exemplary aspect, the MEMS gyrocompass is configured to determine the first fit coefficients individually to each MEMS gyroscope.

According to another exemplary aspect, the second fit coefficients are a cosine coefficient (c) and a sine coefficient (s), and wherein the north angle is calculated by arctan(s/c).

According to another exemplary aspect, the number of MEMS gyroscopes in the MEMS gyrocompass is at least two, and MEMS gyroscopes are arranged such that vector sum of sense axes of the MEMS gyroscopes is zero.

According to another exemplary aspect, the MEMS gyrocompass is configured to simultaneously perform the determination of the first fit coefficients and the second fit coefficients.

Moreover, a computer program product is provided that has instructions which when executed by one or more processing devices of a MEMS gyrocompass to perform the exemplary methods according to the exemplary aspects described above.

According to another exemplary aspect, a computer program product embodied on a non-transitory computer-readable medium is provided, the computer-readable medium comprising instructions stored thereon to cause one or more processing devices of a MEMS gyrocompass to perform the exemplary methods described above.

The exemplary aspects of the present invention are based on the idea of fitting Earth rate response of outputs of a gyroscope array, in other words components of earth rotation rate projected on the reference plane as measured by gyroscopes, as a function of rotation angle at the same time as rate drifts of each gyroscope of the gyroscope array is individually fitted as a function of time. These fittings are preferably performed algorithmically.

Moreover, the exemplary aspects of the present invention provide the advantage to effectively mitigate effects of different offset drift in a plurality of gyroscopes of the gyroscope array, while accuracy of determining north angle and Earth's rotation rate is improved even with a shorter integration time. Furthermore, longer integration times are enabled for further increased accuracy since systematic error caused by rate drifts does not dominate performance of the gyrocompass. Because shorter integration time is required, device warm-up time can be significantly shortened, since also power-on transient effects are mitigated.

BRIEF DESCRIPTION OF THE DRAWINGS

In the following the invention will be described in greater detail, in connection with exemplary embodiments, with reference to the attached drawings, in which.

DETAILED DESCRIPTION

Figure 1:
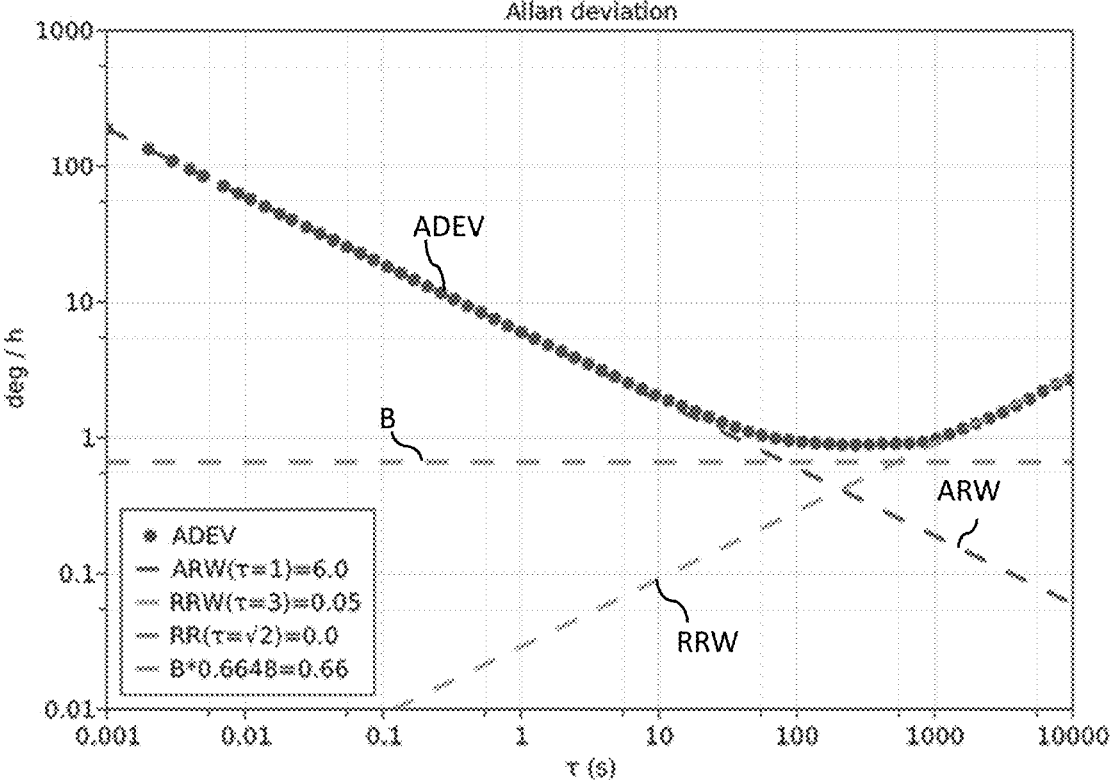
FIG. 1 is an Allan deviation plot of a gyroscope.
Figure 2:
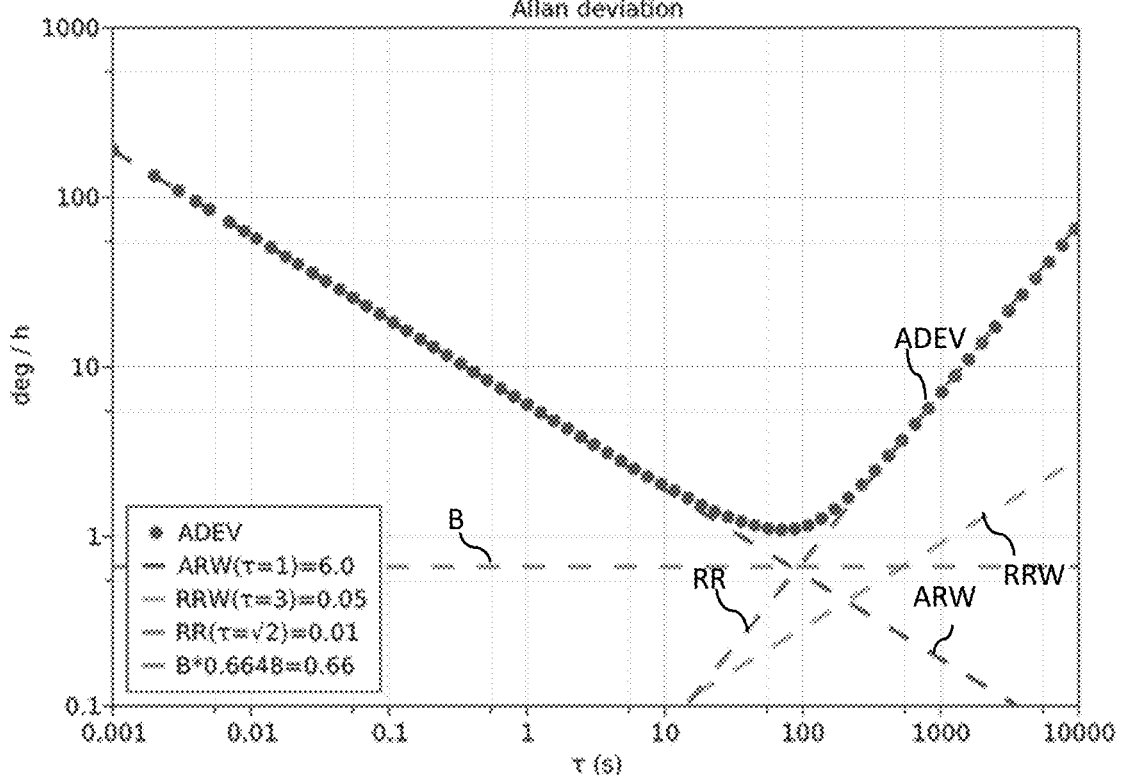
FIG. 2 is another Allan deviation plot of a gyroscope.
Figure 3:
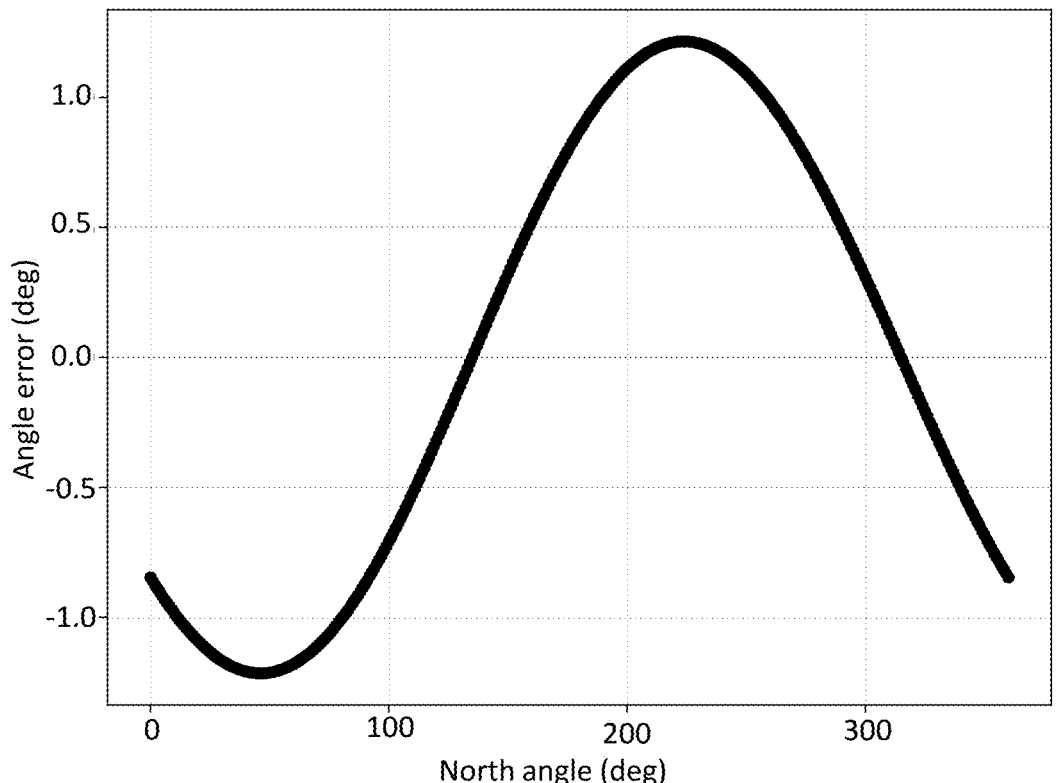
FIG. 3 illustrates angle error of one gyroscope as a function of north angle.
Figure 4:
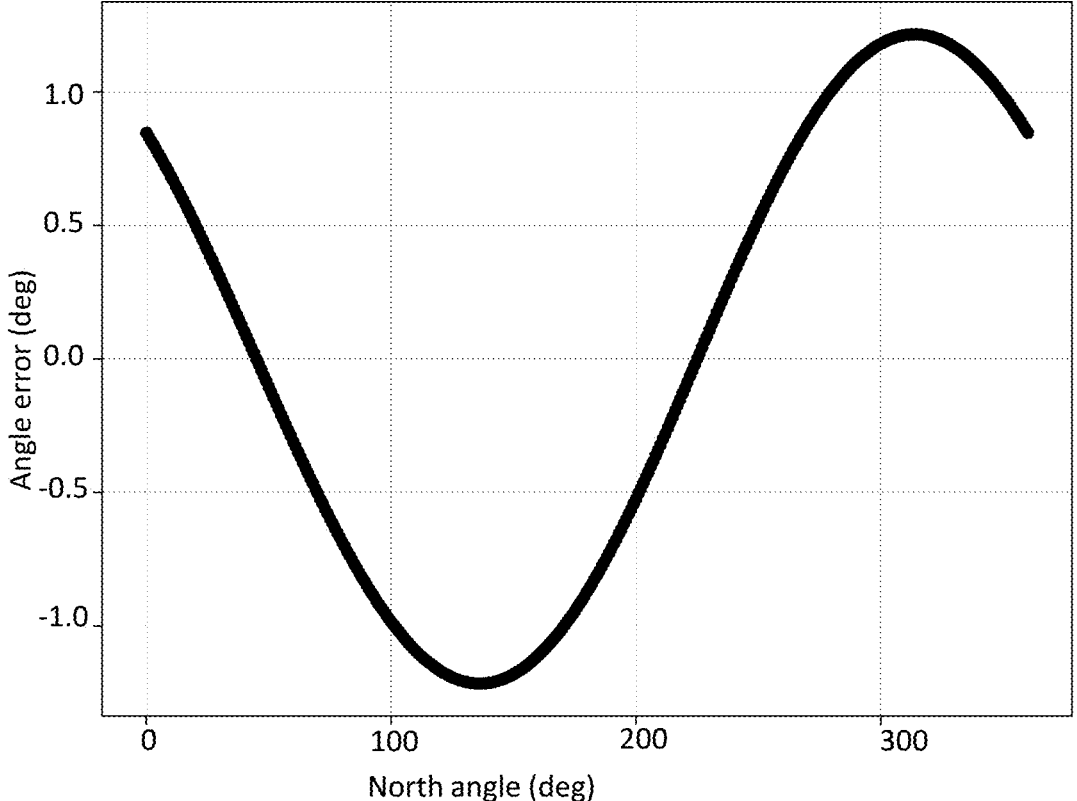
FIG. 4 illustrates angle error of one gyroscope as a function of north angle.
Figure 5:
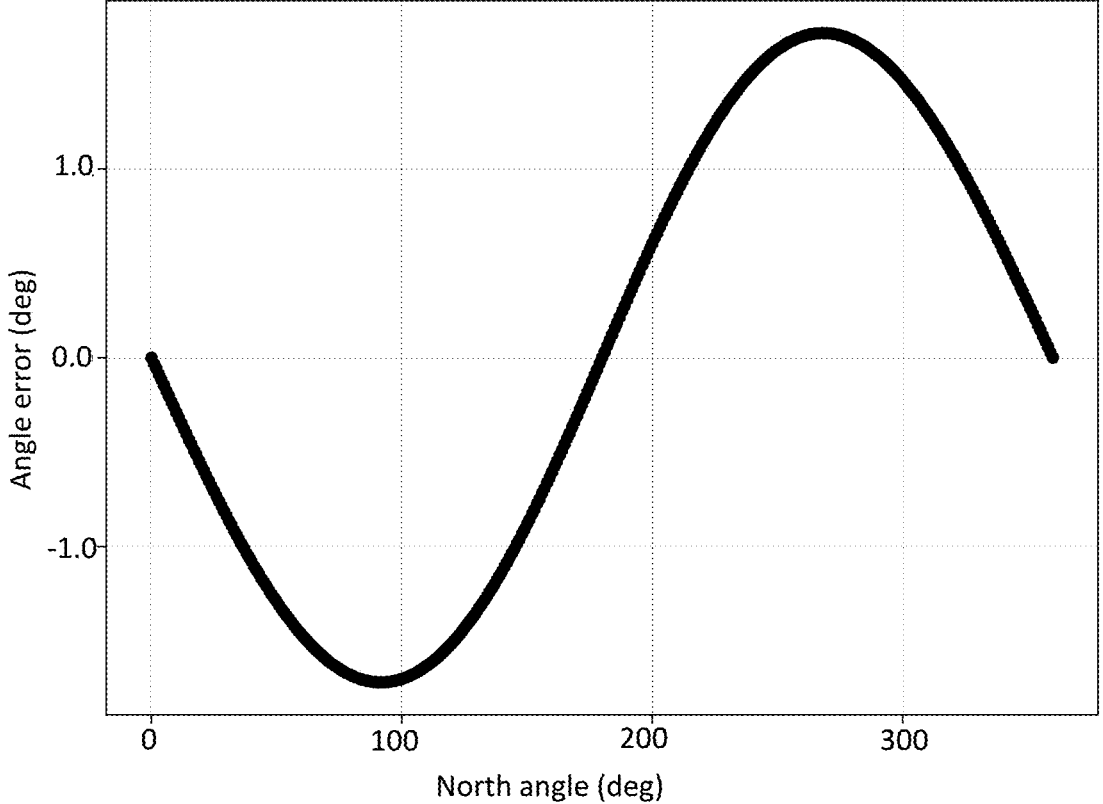
FIG. 5 illustrates north angle error received from two gyroscopes.
Figure 6:
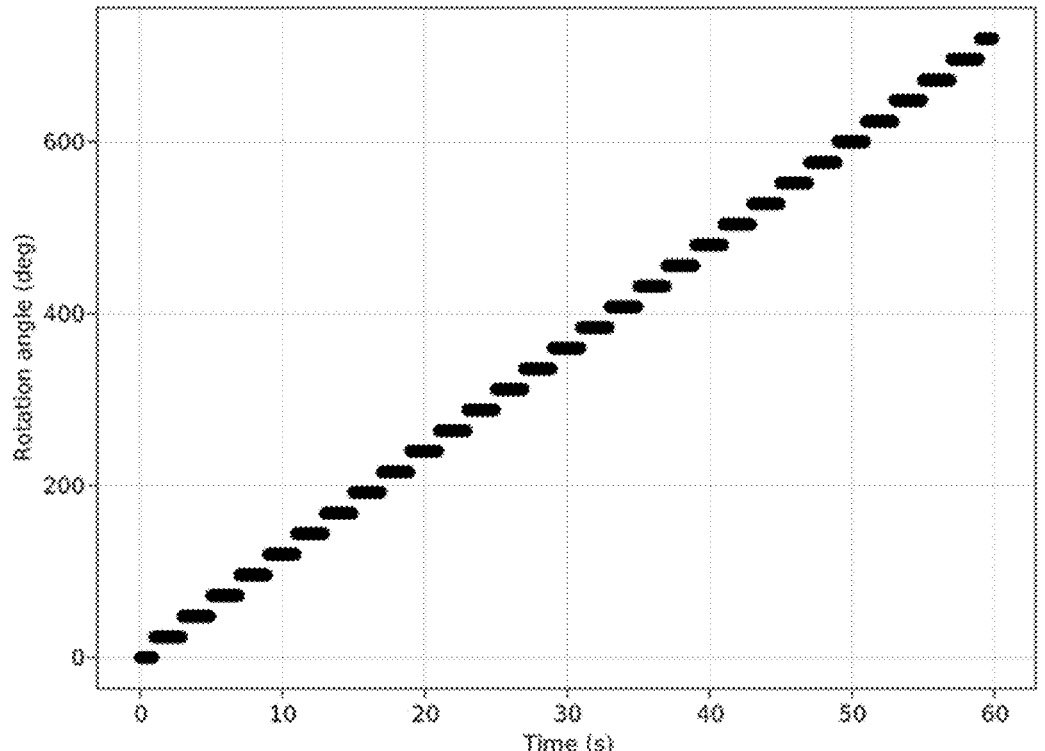
FIG. 6 illustrates stepwise rotation of a turn table.

FIG. 6 illustrates an exemplary stepwise rotation of the turn table that is configured to perform a carouselling operation for a gyroscope. The turn table performs 30 steps of 24° over a duration of one minute (60 s), thus going two full turns (i.e., 720°). It is noted that although technical effects of the invention have been simulated using a turntable setup, the exemplary aspects described herein are applicable with any kind of rotation schemes, which do not have to be known in advance. Only assumption is that rotation occurs with respect to an axis that is orthogonal to the reference plane such that at least two samples are taken at different rotation angles. For example, rotation may be implemented as slow turning of a vehicle in which the MEMS gyrocompass is installed, or the MEMS gyrocompass may be rotated by manually rotating a handheld device comprising the MEMS gyrocompass by an arbitrary, non-zero amount. Moreover, it is noted that although the exemplary aspects of the invention utilize measurement of rotation an axis perpendicular to the reference plane, it is understood that rotation motion may comprise components also deviating from rotation in the reference plane. Effects of such non-useful additional rotation components are omitted by the algorithm described herein.

Figure 7:
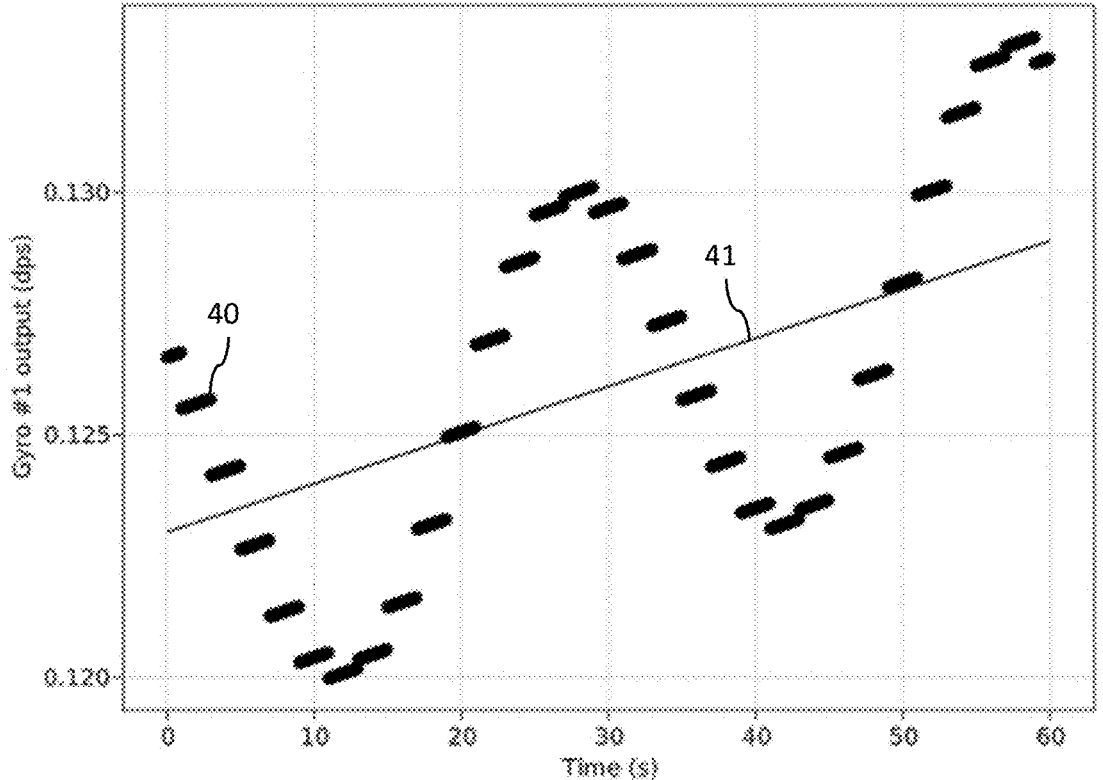
FIG. 7 illustrates linear rate drift.
Figure 8:
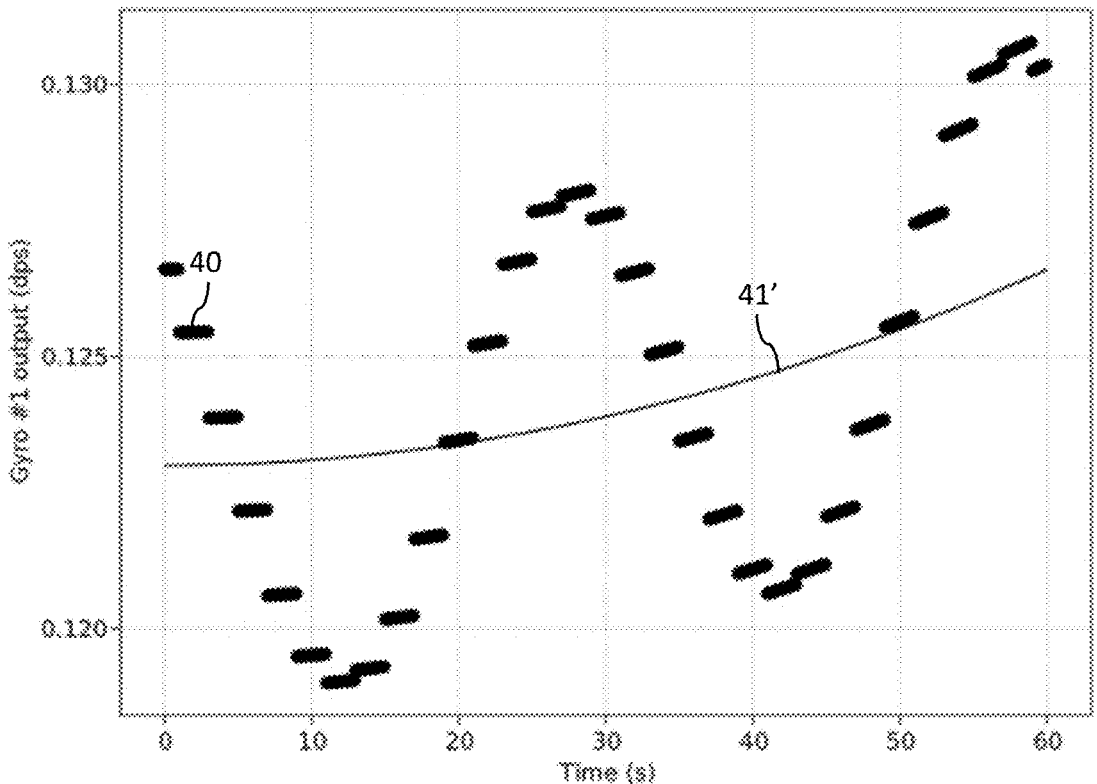
FIG. 8 illustrates quadratic rate drift.

The FIG. 7 illustrates linear rate drift (41) of a single gyroscope. Linear rate drift can be approximated with a first-order equation. When the turn table is rotated, output samples (40) of the gyroscope change at every angle. This can be seen as a sine-like pattern of samples (40) taken of the output signal, here shown over two full turns of the turn table carouselling scheme illustrated in the FIG. 6. Without rate drift, the zero level, minimum and maximum of the intermittent sine pattern formed by the samples (40) would not change over time. However, in this example, there is linear rate drift in phase, which causes the output levels into a constant change.

In this case, rate drift (41) of the gyroscope output can be fitted on a straight line that can be represented with a first-order polynomic function.

FIG. 7 illustrates quadratic rate drift (41') of a single gyroscope, which can be represented with a second-order polynomic function.

Rate drift can also be exponential, in other words it can be best approximated with an exponential function. This may be a single exponential function or a sum of exponential functions. For example, there may be two or more different exponentially behaving rate drifts occurring in the gyroscope, which are characterized with different time constants. With short time intervals, linear fitting likely provides best results. Measured angular rates can in some cases even have no rate drift, even though some bias error still affects the output.

Exemplary rate drift functions can be formulated as follows:

linear: $a_0+a_1t$ exponential (1): $a_0+\alpha_1\exp(-t/\tau_1)$ exponential (2): $a_0+a_1\exp(-t/\tau_1)+a_2\exp(-t/\tau_2)$ quadratic: $a_0+a_1t+a_2t^2$ To avoid overfitting, simple equations such as linear and exponential (1) with single time constant $\tau_1$ are preferred over the more complex quadratic and exponential (2) with two time constants $\tau_1$ and $\tau_2$.

In general, it is noted that the basic algorithm for removing systematic error from output of a gyroscope array with n gyroscopes can be expressed mathematically as a matrix equation. When a polynomic fitting function is used, size of the matrix A has size s×s, where s=2+n(o+1), n refers to number of gyroscopes in the gyroscope array, o is order of rate drift function: o=2 refers to quadratic rate drift function, o=1 refers to linear rate drift function, 0=0 is a constant (no drift). This basic rule of size of the matrix for polynomic fitting is not applicable with exponential fitting functions. Vector y has length s.

An example of the matrix equation applied for a gyrocompass with two gyroscopes and quadratic rate drift function, in other words a rate drift function of an individual gyroscope follows a second order polynomial equation having formula $a_{0,i}+a_{1,i}t+a_{2,i}t^2$, can be represented as:

$$Ay = \begin{pmatrix} \vdots & \vdots & \vdots & \vdots & \vdots & \vdots & \vdots & \vdots \\ \cos(\theta_i+\varphi_1) & \sin(\theta_i+\varphi_1) & 1 & t_i & t_i^2 & 0 & 0 & 0 \\ \cos(\theta_j+\varphi_2) & \sin(\theta_j+\varphi_2) & 0 & 0 & 0 & 1 & t_j & t_j^2 \\ \vdots & \vdots & \vdots & \vdots & \vdots & \vdots & \vdots & \vdots \end{pmatrix} \begin{pmatrix} c \\ s \\ a_{0,1} \\ a_{1,1} \\ a_{2,1} \\ a_{0,2} \\ a_{1,2} \\ a_{2,2} \end{pmatrix} = \begin{pmatrix} \vdots \\ y_{1,i} \\ y_{2,j} \\ \vdots \end{pmatrix} \quad (2)$$

In this equation, $t_i$ refers to a time instance, $\varphi_1$, $\varphi_2$, refer to sense axis angles of gyroscopes on the board with respect to a reference axis within the reference plane, $\theta_i=\theta(t_i)$ refers to board orientation at time instance $t_i$. C and s refer to cosine and sine coefficients that are used to determine the north angle as an angle between the reference axis and the true north, and $a_{0,1}$, $a_{1,1}$, $a_{2,1}$ refer to rate drift coefficients of gyroscope 1. In this example, rate drift function is quadratic, in other words rate drift function of gyroscope 1 follows an equation having formula $a_{0,1}+a_{1,1}t+a_{2,1}t^2$. $y_{1,i}$ refers to gyroscope 1 output at time instance i and $y_{2,j}$ refers to gyroscope 2 output at time instance j.

Rate drift fit coefficients $a_{0,1}$, $a_{1,1}$, $a_{2,1}$ are obtained from $x=A^{-1}y$.

The north angle is calculated from the cosine and sine coefficients c and s by equation:

$$\arctan\frac{s}{c} \quad (3)$$

In-plane component of the Earth's rotation rate in the reference plane is calculated as:

$$\sqrt{s^2+c^2} \quad (4)$$

An example of the matrix equation applied for a gyrocompass with two gyroscopes and exponential rate drift function, in other words a rate drift function of an individual gyroscope follows an exponential equation having formula $a_{0,k}+a_{1,k}e^{\lambda_k t}$, can be represented as follows:

$$\begin{pmatrix} \cos\theta_i & \sin\theta_i & 1 & t_i & \int_0^{t_i}\cos\theta(t)dt & \int_0^{t_i}\sin\theta(t)dt & \int_0^{t_i}y_k(t)dt \\ \cos\theta_j & \sin\theta_i & 1 & t_j & \int_0^{t_j}\cos\theta(t)dt & \int_0^{t_j}\sin\theta(t)dt & \int_0^{t_j}y_k(t)dt \\ \vdots & \vdots & \vdots & \vdots & \vdots & \vdots & \vdots \end{pmatrix} \begin{pmatrix} d_1 \\ d_2 \\ d_3 \\ d_4 \\ d_5 \\ d_6 \\ \lambda_k \end{pmatrix} = \quad (5)$$

$$\begin{pmatrix} y_{k,i} \\ y_{k,j} \\ \vdots \end{pmatrix}$$

wherein $t_i$ is time instance, $\varphi_k$ is orientation of the kth gyro on the board, $\theta(t_i)$ is board orientation at time instance $t_i$, $y_{k,i}$ is gyroscope k output at time instance i. $\int \ldots dt$ is a time integral, evaluated numerically using for example trapezoidal rule or Simpson's rule if the time steps are equal.

Fit coefficients $\lambda_k$ related to time constants $\tau_k=-1/\lambda_k$ are determined using the matrix equation (6) below for every k gyroscope axis, solving it in the least-squares sense. This can be performed by writing equation (5) as Ax=b, least-squares sense means to minimize $\|Ax-bv_2$, where $\|\cdot\|_2$ is a vector norm. The fit coefficient $\lambda_k$ is utilized in further analysis, whereas other coefficients $d_1$, $d_2$, . . . , $d_6$ are not.

$$\begin{pmatrix} \vdots & \vdots & \vdots & \vdots & \vdots & \vdots \\ \cos(\theta_i+\varphi_1) & \sin(\theta_i+\varphi_1) & 1 & e^{\lambda_1 t_i} & 0 & 0 & \ldots \\ \cos(\theta_j+\varphi_2) & \sin(\theta_j+\varphi_2) & 0 & 0 & 1 & e^{\lambda_2 t_j} & \ldots \\ \vdots & \vdots & \vdots & \vdots & \vdots & \vdots \end{pmatrix} \begin{pmatrix} c \\ s \\ a_{0,1} \\ a_{1,1} \\ a_{0,2} \\ a_{1,2} \end{pmatrix} = \begin{pmatrix} \vdots \\ y_{1,i} \\ y_{2,j} \\ \vdots \end{pmatrix} \quad (6)$$

Cosine coefficient c and sine coefficient s are solved in least-squares sense, and north angle and in-plane component of the Earth rate can be calculated as given above in equations (3) and (4).

FIGS. 9A to 11C illustrate effects of the invented algorithm on accuracy of measurements.

Figure 9A:
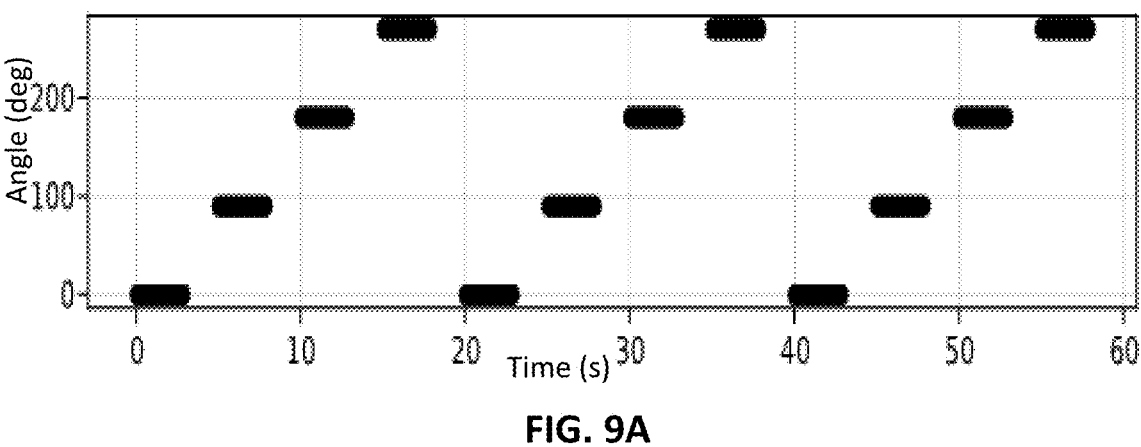
FIG. 9A illustrates step-wise rotation of a turntable.

In particular, FIG. 9A illustrates another example of stepwise rotation of the turn table. The turn table performs 4 steps of 90° over a duration of twenty seconds (20 s), thus going three full turns (1080°) in one minute.

Figure 9B:
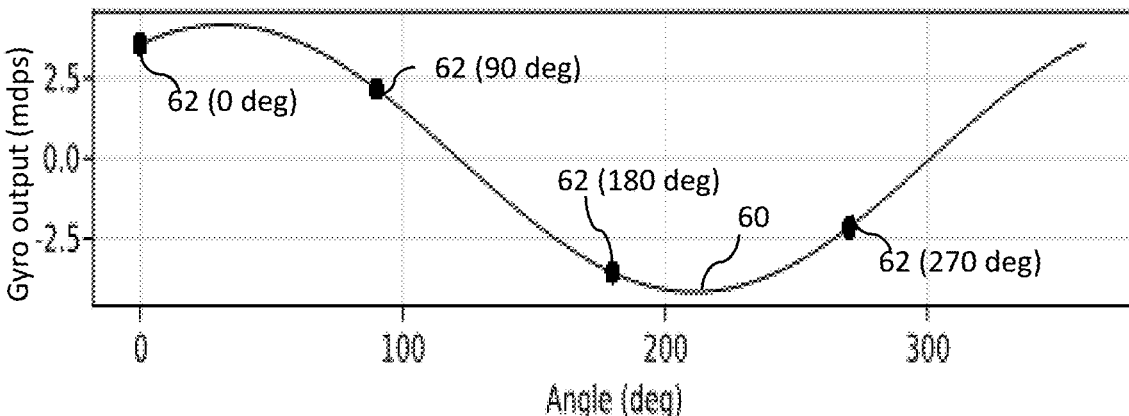
FIG. 9B illustrates output of a single gyroscope without rate drift .

The FIG. 9B illustrates output of a single gyroscope rotated by the turn table as a function angle. In this example, there is no rate drift nor rate drift fitting. Output values (62) of the gyroscope received at the same rotation angle but at different times, in other words during different rotation rounds of the turn table, are the same. In this non-limiting example, each dot representing an output value (62) represents three different measurements. The output values (62) can be easily fitted on a sine curve (60). No systematic error is present and north angle can be accurately determined.

Figure 9C:
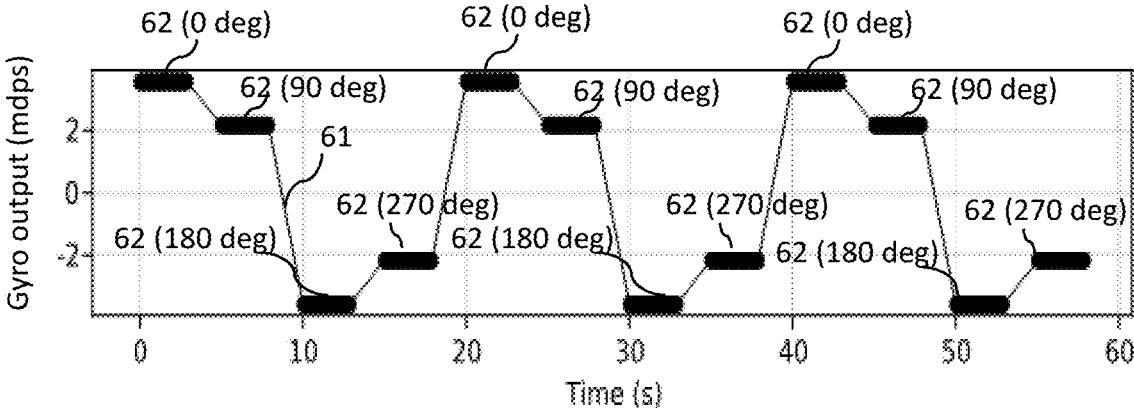
FIG. 9C illustrates gyroscope output as a function of time when no rate drift is present.

Finally, the FIG. 9C illustrates gyroscope output as a function of time, which gives a good view on the total amplitude of the output in mdps (milli-degrees per second).

Tested device in the case 9A to 9C gives a north angle or 31.234 degrees with signal amplitude of 4.178 mdps, which corresponds with theoretic Earth's rotation rate with high accuracy. These values represent the correct reference values for further tests.

Figure 10A:
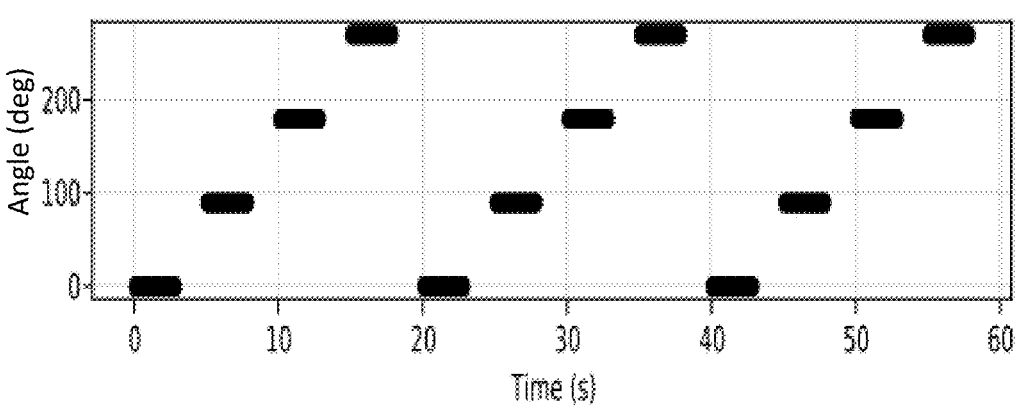
FIG. 10A illustrates step-wise rotation of a turntable.
Figure 10B:
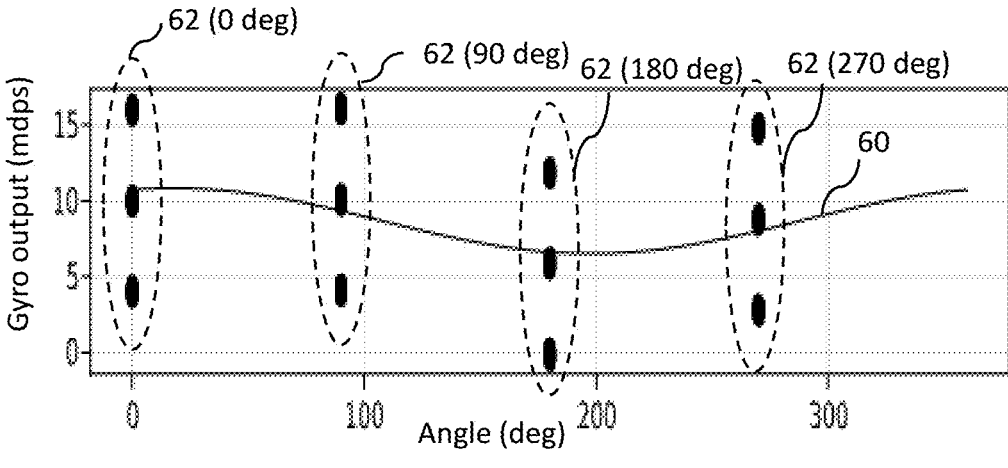
FIG. 10B illustrates different output values of a gyroscope caused by rate drift.
Figure 10C:
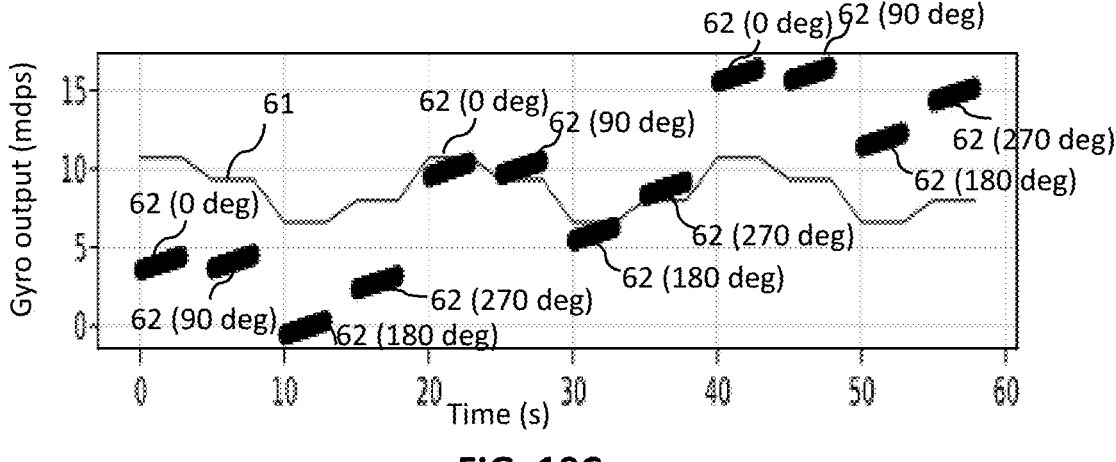
FIG. 10C illustrates gyroscope output with systematic error caused by lack of rate drift fitting.

FIGS. 10A to 10C illustrate the same device as in the FIGS. 9A to 9C. This time there is linear rate drift in place, but no rate drift fitting in time dimension taking place and thus no systematic error correction. For illustration purposes, a strong linear rate drift was applied.

In particular, FIG. 10A shows the stepwise rotation of the turn table, which is the same as shown in the FIG. 9A.

FIGS. 10B and 10C show effects of rate drift in the output of the gyroscope. Because of rate drift, output values (62) of the gyroscope, received at the same rotation angle but at different times, in other words during different rotation rounds of the turn table, are different.

Instead of having a single dot covering all three measurements, the output shown in the FIG. 10B shows three different output values for each turn table angle. In the FIG. 10C output values show three groups on three different levels.

Traditionally fitting is performed by fitting a sine or cosine function to the received rotation rates as shown in the FIG. 10B. The sine or cosine function may be of the form $C*\sin(\alpha_j+\beta)$ or $C*\cos(\alpha_j+\beta)$ respectively, where C is the amplitude of the sine or cosine function, which depends at least on the latitude of the device, $\alpha_j$ is the offset angle of the jth gyroscope's sense axis and $\beta$ is a phase offset, which has a fixed difference with respect to true north, and the heading of the device may be determined by varying the phase offset $\beta$ to find the value with the minimum error in the fit of the sine or cosine function to the received rotation rates. The sine or cosine function may be fit to the received rotation rates using a least-squares mean fitting method or other fitting method.

When output values are averaged over multiple samples (in this example, three samples taken on three intermittently repeated similar rotation table positions), the fitted sine or cosine function as function of angle (60) is way above the zero level. Consequently, the fitted curve as function of time (61) is offset. Using these gyroscope output values in north angle and rotation rate calculations causes a significant systematic error in the result. In this example, with heavy rate drift used for visualization, the north angle value received was 17.77 degrees (compared to the correct 31.234 degrees), thus with significant error of 13.46 degrees, and output amplitude was 2.169 mdps, which has a significant 2 mdps error from the correct value of 4.178 mdps, almost 50%. Such error magnitudes are not acceptable.

Figure 11A:
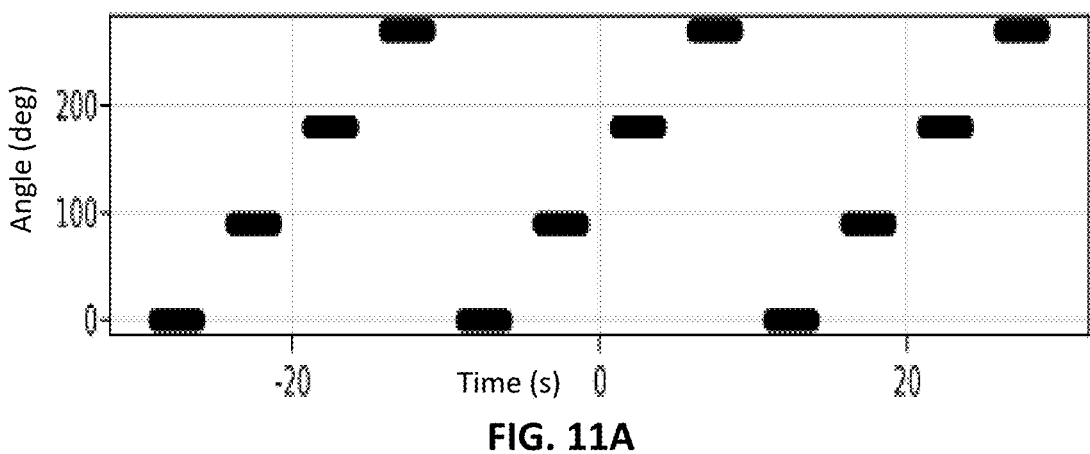
FIG. 11A illustrates step-wise rotation of a turntable.
Figure 11B:
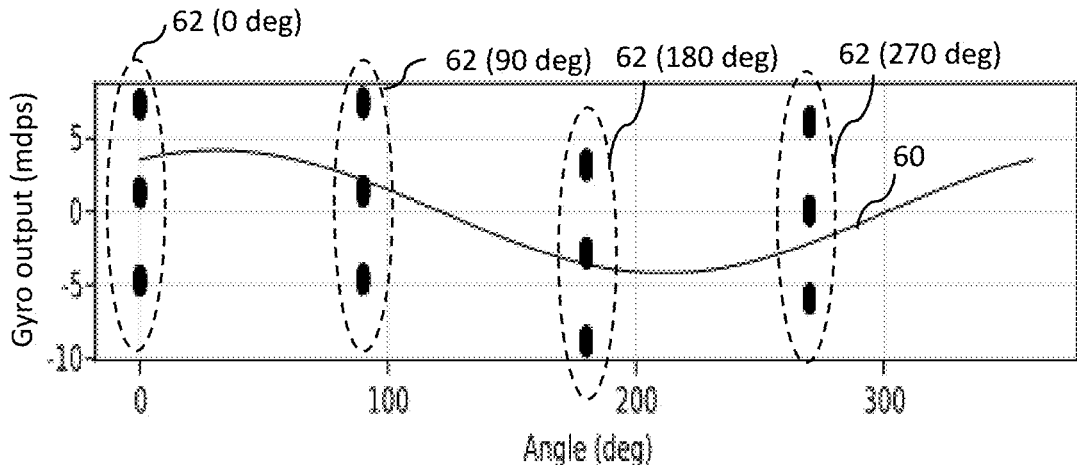
FIG. 11B illustrates different output values of a gyroscope caused by rate drift.
Figure 11C:
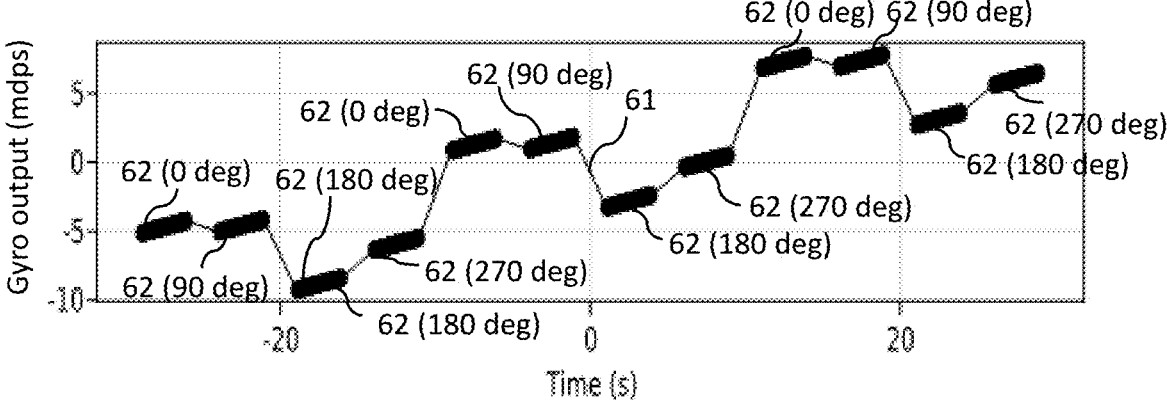
FIG. 11C illustrates gyroscope output with systematic error correction by rate drift fitting.

FIGS. 11A to 11C illustrate the same device as in the FIGS. 9A to 10C, but this time there is linear rate drift. Difference to previously disclosed examples is that rate drift fitting is taking place and thus correction of systematic error is implemented. A linear, first order rate fitting function was applied in this non-limiting example.

In particular, FIG. 11A shows the stepwise rotation of the turn table, which is the same as shown in the FIGS. 9A and 10A.

With proper rate drift fitting taking place, systematic error is removed, and the gyroscope output is brought back zero level as expected.

It should be appreciated that the benefit of performing rate drift fitting as function of time becomes obvious from the FIGS. 11B and 11C. When the linear rate drift of the gyroscope is fitted with a linear rate drift function in time domain, rate drift fitting fully removes effect of rate drift and thus correct output can be obtained. As a result, resulting north angle calculated based on the fitted output as function of time gives a north angle of 31.234 degrees and amplitude (Earth's rotation rate) of 4.169 mdps, both equal to the values received in the non-drift example shown in the FIGS. 9A to 9C.

The angles of the sense axes of the one or more MEMS gyroscopes are preferably angled at regular intervals of 360°/N, where N is the number of sense axes. In case of using single-axis gyroscopes, N is also number of gyroscopes. By applying regular intervals of 360°/N between the sense axes of a plurality of mutually similar gyroscopes, vector sum of sense axes of the gyroscopes is zero.

N may be an even number such that the sense axes of the one or more MEMS gyroscopes are arranged into pairs, wherein the sense axes of each pair of gyroscopes are offset by 180 degrees, thus pairwise zeroing the vector sums of sense axes. N may be an odd number. For example, three gyroscopes with 120° angle between their sense axes produces a zero vector sum.

Figure 12:
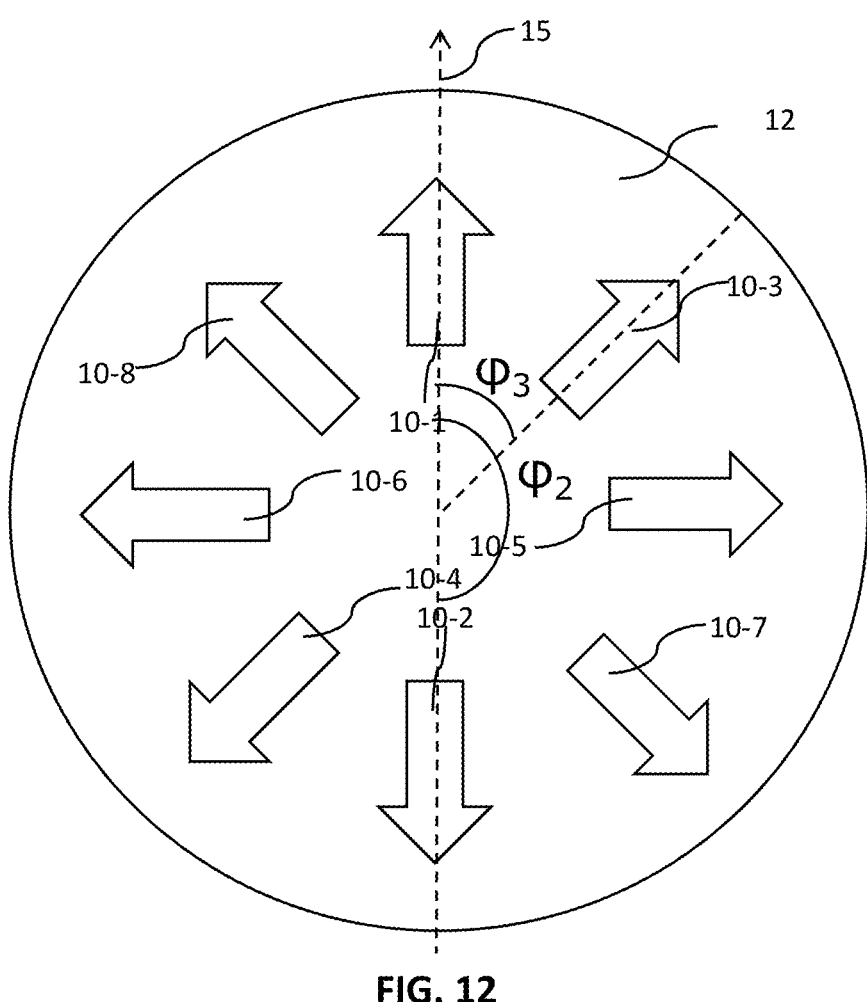
FIG. 12 illustrates a computer simulation platform with eight single-axis gyroscopes.

The algorithm was simulated with a computer simulation platform with eight single-axis gyroscopes (10-1, . . . , 10-8), placed at sense axis angles $\varphi_i=\{0°, 180°, 45°, 225°, 90°, 270°, 135°, 315°\}$ on a rotatable board (12) as schematically illustrated in the FIG. 12. However, computer simulations indicate that three or four gyroscopes and three or four axes already provide good results, while adding more than four gyroscopes and axis provides less significant statistical $1/\sqrt{N}$-improvement. Sense axis of the gyroscopes (10) are illustrated with the direction of the arrow. Sense axis angles $\varphi_j$ are determined in relation to a reference axis (15). Only sense axis angles $\varphi_2=180$ and $\varphi_3=45°$ are shown in the FIG. 12 for clarity. The board (12) was rotated by a turn table that was rotated stepwise to implement carouselling, as illustrated in the FIG. 6. Total sampling time used in the test was 60 seconds, with two full turns (720 degrees). The same algorithm is also applicable with continuous carouselling, with samples taken intermittently at regular time intervals. Although the example in FIG. 12 illustrates gyroscopes (10) arranged radially in a circular pattern, any placement of gyroscopes on the plane of the board is applicable as soon as sense axis angles with respect to a reference axis within the plane of the board (12) remain. Number of gyroscopes may also vary. For example, a single gyroscope may have two orthogonal sense axes, in which case just one gyroscope is needed for sensing two different sense axes. Results of computer simulations are shown in the table 2 below.

TABLE 2

| # | ARW | Time dependency *100e−6 dps/s | Fit time dependency order | mean (deg) | std (deg) |
|---|---|---|---|---|---|
| 1 | 0 | Linear [1, 1, 1, 1, 1, 1, 1, 1] | 0 | 0.000 | 0.00 |
| 2 | 0 | Linear [1, 0, 0, 0, 0, 0, 0, 0] | 0 | 1.38 | 0.00 |
| 3 | 0 | Linear [1, 0, −1, 0, 0, 0, 0, 0] | 0 | 2.23 | 0.00 |
| 4 | 0 | Linear [1, 0, −1, 0, −1, 0, 0, 0] | 0 | 3.59 | 0.00 |
| 5 | 0 | Linear [1, 0, −1, 0, −1, 0, 0, 0] | 1 | 0.000 | 0.00 |
| 6 | 0 | Quadratic [1, 1, 1, 1, 1, 1, 1, 1] | 0 | 0.000 | 0.00 |
| 7 | 0 | Quadratic [1, 0, 0, 0, 0, 0, 0, 0] | 0 | 0.75 | 0.00 |
| 8 | 0 | Quadratic [1, 0, 0, 0, 0, 0, 0, 0] | 1 | −0.084 | 0.00 |
| 9 | 0 | Quadratic [1, 0, 0, 0, 0, 0, 0, 0] | 2 | 0.000 | 0.00 |
| 10 | 0 | Quadratic [1, 1, −1, −1, −1, −1, 1, 1] | 0 | 4.78 | 0.00 |

TABLE 2-continued

| # | ARW | Time dependency *100e−6 dps/s | Fit time dependency order | mean (deg) | std (deg) |
|---|---|---|---|---|---|
| 11 | 0 | Quadratic [−1, −1, −1, −1, 1, 1, 1, 1] | 1 | 0.87 | 0.00 |
| 12 | 0 | Quadratic [−1, −1, −1, −1, 1, 1, 1, 1] | 2 | 0.000 | 0.00 |
| 13 | 0.05 deg/√hr | — | 2 | −0.003 | 0.76 |
| 14 | 0.1 deg/√hr | — | 2 | −0.065 | 1.55 |
| 15 | 0.1 deg/√hr | Linear [1, 0, 0, 0, 0, 0, 0, 0] | 1 | −0.006 | 1.54 |

It is noted that Table 2 illustrates results of computer simulations performed with the invented fitting method using a testbed with eight gyroscopes.

Angular random walk (ARW) was set to zero in the first 12 computer simulations.

Computer simulations #1 to #5 represent examples in which time dependency of rate drift of any individual gyroscope is linear. Nature of time dependency is determined by multipliers 0, 1 and −1, wherein 0 represents no rate drift, and 1 and −1 refer to rate drift in opposite directions.

Computer simulation #1 is a reference case in which all eight gyroscopes have similar linear rate drift. A zero-order fitting function, in other words a constant value is applied as fitting function and averaging samples over the test period removes all errors, mean error in the angle is zero degrees and standard deviation (std) of the error is also zero. Thus, north angle determined based on the measurements is accurate. Although not shown in the table, value of Earth's rotation rate calculated is also accurate.

Computer simulation #2 illustrates a case in which one of the eight gyroscopes has a rate drift pattern that deviates from rate drift of other seven gyroscopes. If a zero order, constant function is used for fitting, mean value of the systematic error in the output is 1.38 degrees. Computer simulations #3 and #4 add further gyroscopes with non-zero linear rate drift characteristics, which further increases the systematic error in the mean value of the output, if a zero-order fitting function is applied. This is apparently not doing a good job for fitting.

Computer simulation #5 applies linear fitting according to the invention in the exemplary case otherwise equal to computer simulation #4. This fitting effectively removes the systematic error in its entirety, and north angle is accurate.

Computer simulations #6 to #12 represent examples in which time dependency of rate drift of an individual gyroscope is quadratic. In other words, the rate drift can be represented by a second-order function.

Computer simulation #6 is a reference in which rate drifts of all gyroscopes are similar. Like in the computer simulation #1, a constant fitting function can be applied and averaging samples over the test period effectively removes all systematic error, mean error in the angle is zero degrees and standard deviation (std) of the systematic error is also zero.

Computer simulations #7, #8 and #9 represent a case in which one of the gyroscopes has a quadratic rate drift while other seven gyroscopes are driftless. In the computer simulation #7, constant value fitting is applied. In the computer simulation #8, linear fitting is applied and in the computer simulation #8 a quadratic fitting is applied. Even the linear fitting (#7) gives fairly good systematic error correction, while using quadratic fitting (#8) in time domain enables fully removing systematic error in the output.

Computer simulations #10, #11 and #12 represent a case in which all gyroscopes have quadratic rate drifts, but in different directions. Constant fitting (#10) leaves a significant systematic error in the output. Use of linear fitting (#11) reduces output systematic error to less than one degree, while use of quadratic fitting (#12) effectively removes all systematic error in the output and also has zero standard deviation.

Computer simulations #13, #14 and #15 represent a situation with angular random walk (ARW) is present. Computer simulations #13 and #14 indicate that with second order rate fitting, also effects of white noise can effectively be mitigated, although some standard deviation remains in the result due to sporadic characteristic of the ARW. Computer simulation #15 indicates that even if there is a gyroscope that has linear rate drift in addition to presence of ARW, linear fitting can effectively remove all systematic error from the output.

It is noted that the exemplary fitting algorithm as described herein not only enables removing systematic error. In particular, the algorithm also enables shortening integration times required for removing effects of angular random walk and using longer integration times, since effects of rate drifts do not dominate performance even if integration time is long. Thus, waiting time for receiving relatively accurate north angle information during warm-up time of the device can be shortened.

The algorithm was found to be effective even with just two gyroscopes, especially when there is a 180-degree offset angle between their sense axes. However, when designing an actual functional gyrocompass, other error causing phenomena should be taken into account. For improving effect of angular random walk (ARW), it is preferred to have more than two gyroscopes, preferably arranged such that vector sum of sense axes is zero. An embodiment with three gyroscopes arranged at 120-degree angles between their sense axes has a vector sum equal to zero always has at least two gyroscopes providing a non-zero signal. Another embodiment is to arrange gyroscopes pairwise such that sense axes in each pair are offset by 180 degrees, which provides strongest possible output signal and thus has the best signal-to-noise ratio.

Figure 13:
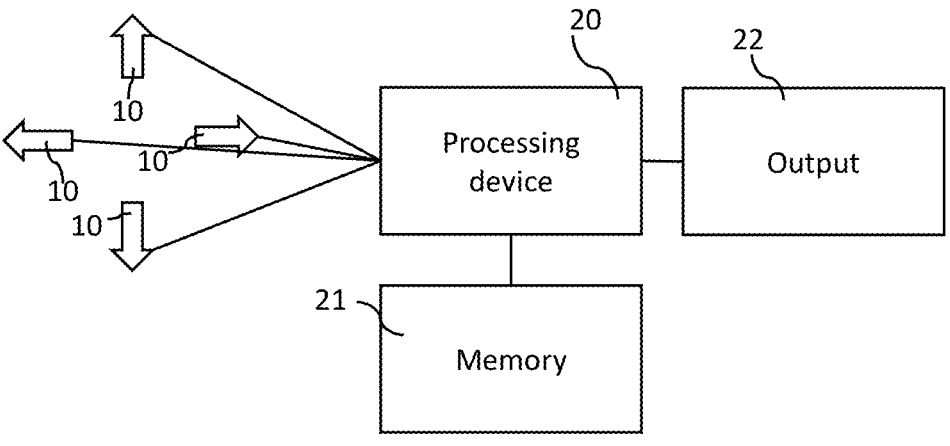
FIG. 13 is a schematic presentation of functional elements of a MEMS gyrocompass.

FIG. 13 illustrates schematically main functional elements of an exemplary MEMS gyrocompass according to an exemplary aspect. The MEMS gyrocompass comprises MEMS gyroscopes (10), at least one processing device (20) arranged in communication with the MEMS gyroscopes (10) and configured to obtain samples of outputs of the MEMS gyroscopes (10). Number of MEMS gyroscopes (10) is a design option according to exemplary aspects, but specific arrangements of the MEMS gyroscopes (10) have been recognized to have different technical benefits. The processing device (20) is communicatively coupled to a memory (21) comprising code which, when executed by the processing device (20) processes samples obtained from the outputs of the MEMS gyroscopes (10) to perform the exemplary algorithms described herein and thus provide an indication of north angle at an output (22).

In general, it is noted that the exemplary embodiments described above are intended to facilitate the understanding of the present invention and are not intended to limit the interpretation of the present invention. The present invention may be modified and/or improved without departing from the spirit and scope thereof, and equivalents thereof are also included in the present invention. That is, exemplary embodiments obtained by those skilled in the art applying design change as appropriate on the embodiments are also included in the scope of the present invention as long as the obtained embodiments have the features of the present invention. For example, each of the elements included in each of the embodiments, and arrangement, materials, conditions, shapes, sizes, and the like thereof are not limited to those exemplified above and may be modified as appropriate. It is to be understood that the exemplary embodiments are merely illustrative, partial substitutions or combinations of the configurations described in the different embodiments are possible to be made, and configurations obtained by such substitutions or combinations are also included in the scope of the present invention as long as they have the features of the present invention.

What is claimed:

1. A method for mitigating systematic error in north angle determined by a MEMS gyrocompass that includes at least one MEMS gyroscope having a sense axis within a reference plane, the method comprising:

obtaining samples from an output of the at least one MEMS gyroscope in at least two different angles of rotation about an axis perpendicular to the reference plane;

fitting an Earth rate response of the output as a function of a rotation angle simultaneously with individually fitting rate drift of each MEMS gyroscope of the at least one MEMS gyroscope as a function of time, wherein the fittings is performed by:

determining one or more first fit coefficients ($a_0$, $a_1$; $a_0$, $a_1$, $\tau_1$, $a_0$, $a_1$, $\tau_1$, $a_2$, $\tau_2$; $a_0$, $a_1$, $a_2$) by fitting samples obtained from each individual MEMS gyroscope with at least one function determined as the function of time, and determining cosine and sine coefficients by fitting components of an Earth rotation rate projected on the reference plane based on samples obtained from each of the at least one MEMS gyroscope with at least one function determined from the rotation angle of the at least one MEMS gyroscope with respect to a reference angle; and determining the north angle as an angle between the reference angle and true north based on the cosine and sine coefficients.

2. The method according to claim 1, wherein the at least one first function determined as the function of time is a rate drift fitting function.

3. The method according to claim 2, wherein the rate drift fitting function is one of a first order function, a second order function, an exponential function and a sum of exponential functions.

4. The method according to claim 3, further comprising fitting the samples using any one of the rate drift fitting functions individually for each MEMS gyroscope.

5. The method according to claim 1, further comprising calculating the north angle by arctan (sine coefficient/cosine coefficient).

6. The method according to claim 1, wherein the at least one MEMS gyroscope comprises two or more MEMS gyroscopes that are arranged such that a vector sum of sense axes of the respective two or more MEMS gyroscopes is zero.

7. The method according to claim 1, wherein the determining of the first fit coefficients and the cosine and sine coefficients are performed simultaneously.

8. A MEMS gyrocompass for mitigating systematic error in determination of a north angle, the MEMS gyrocompass comprising:

at least one MEMS gyroscope having a sense axis within a reference plane;

a memory; and a processing device communicatively coupled to the memory and that is configured to execute code on the memory that configures the processing device to:

obtain samples from an output of the at least one MEMS gyroscope in at least two different angles of rotation about an axis perpendicular to the reference plane;

fit an Earth rate response of the output as a function of a rotation angle simultaneously with individually fitting rate drift of each MEMS gyroscope of the at least one MEMS gyroscope as a function of time, wherein the processing device further determines the fittings by:

determining one or more first fit coefficients ($a_0$, $a_1$; $a_0$, $a_1$, $\tau_1$, $a_2$, $\tau_2$; $a_0$, $a_1$, $a_2$) by fitting samples obtained from each individual MEMS gyroscope with at least one function determined as the function of time, and determining cosine and sine coefficients by fitting components of an Earth rotation rate projected on the reference plane based on samples obtained from each of the at least one MEMS gyroscope with at least one function determined as the function of from the rotation angle of the at least one MEMS gyroscope with respect to a reference angle; and wherein the processing device of the MEMS gyrocompass is further configured to determine the north angle as an angle between the reference angle and true north based on the cosine and sine coefficients.

9. The MEMS gyrocompass according to claim 8, wherein the at least one function determined as the function of time is a rate drift fitting function.

10. The MEMS gyrocompass according to claim 9, wherein the rate drift fitting function is one of a first order function, a second order function, an exponential function and a sum of exponential functions.

11. The MEMS gyrocompass according to claim 10, wherein the processing device is further configured to fit the samples using any one of the rate drift fitting functions individually for each MEMS gyroscope.

12. The MEMS gyrocompass according to claim 8, wherein the north angle is calculated by arctan (sine coefficient/cosine coefficient).

13. The MEMS gyrocompass according to claim 8, wherein the at least one MEMS gyroscope comprises two or more MEMS gyroscopes that are arranged such that a vector sum of sense axes of the respective two or more MEMS gyroscopes is zero.

14. The MEMS gyrocompass according to claim 8, wherein the processing device is further configured to determine the first fit coefficients and the cosine and sine coefficients simultaneously.

15. A computer program product comprising a non-transitory computer readable medium storing code with instructions executable by a processing device for mitigating systematic error in north angle determined by a MEMS gyrocompass that includes at least one MEMS gyroscope having a sense axis within a reference plane, comprising:

code for obtaining samples from an output of the at least one MEMS gyroscope in at least two different angles of rotation about an axis perpendicular to the reference plane;

code for fitting an Earth rate response of the output as a function of a rotation angle simultaneously with individually fitting rate drift of each MEMS gyroscope of the at least one MEMS gyroscope as a function of time, wherein the fittings is performed by:

determining one or more first fit coefficients ($a_0$, $a_1$; $a_0$, $a_1$, $\tau_1$; $a_0$, $a_1$, $\tau_1$, $a_2$, $\tau_2$; $a_0$, $a_1$, $a_2$) by fitting samples obtained from each individual MEMS gyroscope with at least one determined as the function of time, and determining cosine and sine coefficients by fitting components of an Earth rotation rate projected on the reference plane based on samples obtained from all of the at least one MEMS gyroscope with at least one function determined as from the rotation angle of the at least one MEMS gyroscope with respect to a reference angle; and code for determining the north angle as an angle between the reference angle and true north based on the cosine and sine coefficients.

16. The computer program product according to claim 15, wherein the at least one first fitting function is a rate drift fitting function, which is one of a first order function, a second order function, an exponential function and a sum of exponential functions.

17. The computer program product according to claim 16, further comprising code for fitting the samples using any one of the rate drift fitting functions individually for each MEMS gyroscope.

18. The computer program product according to claim 16, wherein the north angle is calculated by arctan (sine coefficient/cosine coefficient).

19. The computer program product according to claim 16, wherein the at least one MEMS gyroscope comprises two or more MEMS gyroscopes that are arranged such that a vector sum of sense axes of the respective two or more MEMS gyroscopes is zero.

20. The computer program product according to claim 16, further comprising code for determining the first fit coefficients and the cosine and sine coefficients simultaneously.

* * * * *